(12) United States Patent
Faller et al.

(10) Patent No.: US 7,160,905 B2
(45) Date of Patent: Jan. 9, 2007

(54) HYDROXYETHYLENE COMPOUNDS WITH ASP2 INHIBITORY ACTIVITY

(75) Inventors: Andrew Faller, Windlesham (GB); Peter Henry Milner, Harlow (GB); John Gerard Ward, Harlow (GB)

(73) Assignee: SmithKline Beecham p.l.c., Brentford (GB)

( * ) Notice: Subject to any disclaimer, the term of this patent is extended or adjusted under 35 U.S.C. 154(b) by 92 days.

(21) Appl. No.: 10/496,334

(22) PCT Filed: Nov. 29, 2002

(86) PCT No.: PCT/EP02/13517

§ 371 (c)(1),
(2), (4) Date: Oct. 5, 2004

(87) PCT Pub. No.: WO03/045903

PCT Pub. Date: Jun. 5, 2003

(65) Prior Publication Data

US 2005/0038028 A1    Feb. 17, 2005

(30) Foreign Application Priority Data

Nov. 30, 2001  (GB) ................... 0128746.5
Nov. 30, 2001  (GB) ................... 0128747.3
Jun. 18, 2002  (GB) ................... 0214088.7

(51) Int. Cl.
*A61K 31/44*  (2006.01)
*A61K 31/41*  (2006.01)
*C07D 211/72*  (2006.01)
*C07D 333/12*  (2006.01)
*C07D 207/40*  (2006.01)

(52) U.S. Cl. ............ 514/347; 514/359; 514/424; 514/676; 549/74; 548/546

(58) Field of Classification Search ........... 549/74; 514/359, 347, 424, 676, 294, 546; 546/294; 548/546

See application file for complete search history.

(56) References Cited

FOREIGN PATENT DOCUMENTS

WO    WO 01/70672    9/2001

OTHER PUBLICATIONS

Citron et. al., "Human Beta-Secretase and Alzheimer's Disease", Expert Opinion Therapeutic Patents (2001) 5(3):341-346.*
Jhee et. al., "B-Amyloid Therapies in Alzheimer's Disease", Expert Opinion on Investigational Drugs (2001) 10(4):593-605.*

* cited by examiner

*Primary Examiner*—Thomas McKenzie
*Assistant Examiner*—Binta Robinson
(74) *Attorney, Agent, or Firm*—Bonnie L. Deppenbrock

(57) ABSTRACT

The present invention relates to novel hydroxyethylene compounds having Asp2 (β-secretase. BACE1 or Memapsin) inhibitory activity, processes for their preparation, to compositions containing them and to their use in the treatment of diseases characterised by elevated β-amyloid levels or β-amyloid deposits, particularly Alzheimer's disease.

4 Claims, No Drawings

HYDROXYETHYLENE COMPOUNDS WITH ASP2 INHIBITORY ACTIVITY

This application is filed pursuant to 35 U.S.C. § 371 as a United States National Phase Application of International Application No. PCT/EP02/13517 filed Nov. 29, 2002, which claims priority from GB0128747.3 filed Nov. 30, 2001 and GB0128746.5 filed Nov. 30, 2001 and GB0214088.7 filed Jun. 18, 2002.

The present invention relates to novel hydroxyethylene compounds having Asp2 (β-secretase, BACE1 or Memapsin) inhibitory activity, processes for their preparation, to compositions containing them and to their use in the treatment of diseases characterised by elevated β-amyloid levels or β-amyloid deposits, particularly Alzheimer's disease.

Alzheimer's disease is a degenerative brain disorder in which extracellular deposition of Aβ in the form of senile plaques represents a key pathological hallmark of the disease (Selkoe, D. J. (2001) Physiological Reviews 81: 741–766). The presence of senile plaques is accompanied by a prominent inflammatory response and neuronal loss. Aβ exists in soluble and insoluble, fibrillar forms and a specific fibrillar form has been identified as the predominant neurotoxic species (Vassar, R. and Citron, M. (2000) Neuron 27: 419–422). In addition it has been reported that dementia correlates more closely with the levels of soluble amyloid rather than plaque burden (Naslund, J. et al. (2000) J. Am. Med. Assoc. 12: 1571–1577; Younkin, S. (2001) Nat. Med. 1: 8–19). Aβ is known to be produced through the cleavage of the beta amyloid precursor protein (also known as APP) by an aspartyl protease enzyme known as Asp2 (also known as β-secretase, BACE1 or Memapsin) (De Strooper, B. and Konig, G. (1999) Nature 402: 471–472).

Therefore, it has been proposed that inhibition of the Asp2 enzyme would reduce the level of APP processing and consequently reduce the levels of Aβ peptides found within the brain. Therefore, it is also thought that inhibition of the Asp2 enzyme would be an effective therapeutic target in the treatment of Alzheimer's disease.

APP is cleaved by a variety of proteolytic enzymes (De Strooper, B. and Konig, G. (1999) Nature 402: 471–472). The key enzymes in the amyloidogenic pathway are Asp2 (β-secretase) and γ-secretase both of which are aspartic proteinases and cleavage of APP by these enzymes generates Aβ. The non-amyloidogenic, α-secretase pathway, which precludes Aβ formation, has been shown to be catalysed by a number of proteinases, the best candidate being ADAM10, a disintegrin and metalloproteinase. Asp1 has been claimed to show both α- and β-secretase activity in vitro. The pattern of expression of Asp1 and Asp2 are quite different, Asp2 is most highly expressed in the pancreas and brain while Asp1 expression occurs in many other peripheral tissues. The Asp2 knockout mouse indicates that lack of Asp2 abolished Aβ production and also shows that in this animal model endogenous Asp1 cannot substitute for the Asp2 deficiency (Luo, Y. et al. (2001) Nat Neurosci. 4: 231–232; Cai, H. et. al. (2001) Nat Neurosci. 4: 233–234; Roberds, S. L. et al. (2001) Hum. Mol. Genet. 10: 1317–1324).

For an agent to be therapeutically useful in the treatment of Alzheimer's disease it is preferable that said agent is a potent inhibitor of the Asp2 enzyme, but should ideally also be selective for Asp2 over other enzymes of the aspartyl proteinase family, e.g Cathepsin D (Connor, G. E. (1998) Cathepsin D in Handbook of Proteolytic Enzymes, Barrett, A. J., Rawlings, N. D., & Woesner, J. F. (Eds) Academic Press London. pp828–836)

WO 01/70672 (Elan Pharmaceuticals Inc.) describe a series of hydroxyethylene compounds having β-secretase activity which are implicated to be useful in the treatment of Alzheimer's disease.

We have found a novel series of compounds which are potent inhibitors of the Asp2 enzyme, thereby indicating the potential for these compounds to be effective in the treatment of Alzheimer's disease.

Thus, according to a first aspect of the present invention we provide a compound of formula (I):

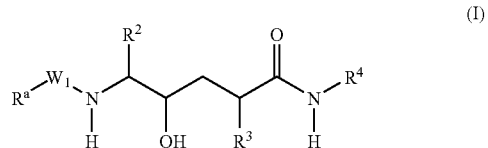

wherein $R^a$ represents a group of formula (a):

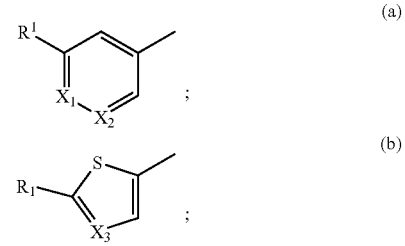

or a group of formula (b):

$R^1$ represents —$SO_2R^5$;
$R^5$ represents methyl or ethyl;
$X_1$ represents N, —C(—$R^6$)— or —C(—O—$R^7$)—;
$X_2$ and $X_3$ independently represent N, —C(—$R^8$)— or —C(—Y—$R^9$)—;
Y represents a bond, $CH_2$, O, S, CO, $NR^{10}$, —N($R^{10}$)C(O)—, —C(O)N($R^{10}$)—, COO, aryl, heterocyclyl or heteroaryl;
$R^6$ represents hydrogen, halogen, —$C_{1-6}$ alkyl, —$C_{2-4}$ alkenyl, —$C_{3-8}$ cycloalkyl, —$C_{1-2}$ alkyl-$C_{3-8}$ cycloalkyl, heteroaryl, heterocyclyl or aryl;
$R^8$ represents halogen;
$R^7$, $R^9$ and $R^{10}$ independently represent hydrogen, —$C_{1-6}$ alkyl, —$C_{2-6}$ alkenyl, —$C_{3-8}$ cycloalkyl, —$C_{1-2}$ alkyl-$C_{3-8}$ cycloalkyl, heteroaryl, heterocyclyl or aryl;
$W_1$ represents CO or $SO_2$;
$R^2$ represents —$C_{5-8}$ alkyl, —$C_{1-6}$ alkyl-aryl, —$C_{1-6}$ alkyl-heteroaryl, —$C_{1-6}$ alkyl-heterocyclyl, —$C_{1-6}$ alkyl-$C_{3-8}$ cycloalkyl, —$C_{1-6}$ alkyl-S-aryl, —$C_{1-6}$ alkyl-O-aryl, —$C_{1-6}$ alkyl-S-heteroaryl or —$C_{1-6}$ alkyl-O-heteroaryl;
$R^3$ represents —$C_{1-6}$ alkyl or propargyl;
$R^4$ represents —$C_{1-6}$ alkyl, —$C_{1-6}$ alkyl-aryl, —$C_{1-6}$ alkyl-heteroaryl, —$C_{1-6}$ alkyl-heterocyclyl, —$C_{3-8}$ cycloalkyl, —$C_{1-6}$ alkyl-$C_{3-8}$ cycloalkyl or propargyl;

or a pharmaceutically acceptable salt or solvate thereof.

References to alkyl include references to both straight chain and branched chain aliphatic isomers of the corresponding alkyl. It will be appreciated that references to alkenyl shall be interpreted similarly. It will also be appreciated that alkyl may be optionally substituted with one or more, preferably 1 to 3, halogen atoms, hydroxy, —COOH, —COOCH$_3$, alkoxy, cyano or amino groups.

References to C$_{3-8}$ cycloalkyl include references to all alicyclic (including branched) isomers of the corresponding alkyl. It will be appreciated that cycloalkyl may be optionally substituted with one or more, preferably 1 to 3, halogen atoms, hydroxy, —COOH, —COOCH$_3$, alkoxy, cyano or amino groups.

References to 'aryl' include references to monocyclic carbocyclic aromatic rings (eg. phenyl) and bicyclic carbocyclic aromatic rings (e.g. naphthyl).

References to 'heteroaryl' include references to mono- and bicyclic heterocyclic aromatic rings containing 1–4 hetero atoms selected from nitrogen, oxygen and sulphur. Examples of monocyclic heterocyclic aromatic rings include e.g. thienyl, furyl, pyrrolyl, triazolyl, imidazolyl, oxazolyl, thiazolyl, oxadiazolyl, isothiazolyl, isoxazolyl, thiadiazolyl, pyrazolyl, pyrimidyl, pyridazinyl, pyrazinyl, pyridyl, tetrazolyl and the like. Examples of bicyclic heterocyclic aromatic rings include eg. quinolinyl, isoquinolinyl, quinazolinyl, quinoxalinyl, cinnolinyl, naphthyridinyl, indolyl, indazolyl, pyrrolopyridinyl, benzofuranyl, benzothienyl, benzimidazolyl, benzoxazolyl, benzisoxazolyl, benzothiazolyl, benzisothiazolyl, benzoxadiazolyl, benzothiadiazolyl and the like.

References to 'heterocyclyl' include references to a 5–7 membered non-aromatic monocyclic ring containing 1 to 3 heteroatoms selected from nitrogen, sulphur or oxygen. Examples of heterocyclic non-aromatic rings include morpholinyl, piperidinyl, piperazinyl, thiomorpholinyl, oxathianyl, dithianyl, dioxanyl, pyrrolidinyl, dioxolanyl, oxathiolanyl, imidazolidinyl, pyrazolidinyl and the like.

Carbocyclic and heterocyclic aromatic and non-aromatic heterocyclic rings may be optionally substituted, e.g. by one or more, preferably 1 to 3, C$_{1-6}$ alkyl, C$_{2-6}$ alkenyl, halogen, C$_{1-6}$ alkoxy, CN, hydroxy, oxo, nitro, —NHCOC$_{1-6}$ alkyl, —OCF$_3$, —CF$_3$, —COOH, —COOC$_{1-6}$ alkyl, —OCHF$_2$, —SCF$_3$, —NR$^{11}$R$^{12}$, —CONR$^{11}$R$^{12}$, —SO$_2$NR$^{11}$R$^{12}$ (wherein R$^{11}$ and R$^{12}$ independently represent hydrogen, C$_{1-6}$ alkyl or C$_{3-8}$ cycloalkyl), —NHSO$_2$CH$_3$, —SO$_2$CH$_3$ or —SCH$_3$ groups.

Preferably, R$^5$ represents methyl.
Preferably, X$_1$ represents —C(H)— or N.
Preferably, X$_2$ represents —C(—Y—R$^9$)—.
Preferably, X$_3$ represents —C(H)—.
Preferably, Y represents a bond, O, S or CO, more preferably O.
Preferably, R$^9$ represents hydrogen, —C$_{1-6}$ alkyl, heterocyclyl (particularly 2-oxopyrrolidin-1-yl) or aryl, more preferably —C$_{1-6}$ alkyl, heterocyclyl or aryl.
When Y represents a bond, R$^9$ is preferably hydrogen or heterocyclyl (particularly 2-oxopyrrolidin-1-yl).
When Y represents O, R$^9$ is preferably —C$_{1-6}$ alkyl (particularly methyl or propyl).
Preferably, W$_1$ represents CO.
Preferably, R$^2$ represents benzyl optionally substituted with one or more halogen atoms (eg. fluorine).
Preferably, R$^3$ represents methyl, 3-methyl butyl or propargyl, more preferably methyl.
Preferably, R$^4$ represents —C$_{1-6}$ alkyl (particularly 3,3-dimethyl butyl), —C$_{3-8}$ cycloalkyl (particularly norbornyl or cyclohexyl) each of which may be optionally substituted with a COOH group, or propargyl.

Preferred compounds according to the invention include examples E1–E9 as shown below, or a pharmaceutically acceptable salt thereof.

The compounds of formula (I) can form acid addition salts thereof. It will be appreciated that for use in medicine the salts of the compounds of formula (I) should be pharmaceutically acceptable. Suitable pharmaceutically acceptable salts will be apparent to those skilled in the art and include those described in J. Pharm. Sci., 1977, 66, 1–19, such as acid addition salts formed with inorganic or organic acids e.g. hydrochlorides, hydrobromides, sulphates, phosphates, acetates, benzoates, citrates, nitrates, succinates, lactates, tartrates, fumarates, maleates, 1-hydroxy-2-naphthoates, palmoates, methanesulphonates, p-toluenesulphonates, naphthalenesulphonates, formates or trifluoroacetates. The present invention includes within its scope all possible stoichiometric and non-stoichiometric forms.

The compounds of formula (I) may be prepared in crystalline or non-crystalline form, and, if crystalline, may optionally be solvated, eg. as the hydrate. This invention includes within its scope stoichiometric solvates (eg. hydrates) as well as compounds containing variable amounts of solvent (eg. water).

Certain compounds of formula (I) are capable of existing in stereoisomeric forms (e.g. diastereomers and enantiomers) and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof. Preferably, compounds of formula (I) are in the form of a single enantiomer of formula (Ia):

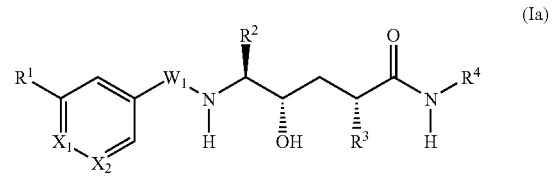

(Ia)

The compounds of formula (I) and salts and solvates thereof may be prepared by the methodology described hereinafter, constituting a further aspect of this invention.

A process according to the invention for preparing a compound of formula (I) which comprises:
(a) reacting a compound of formula (II)

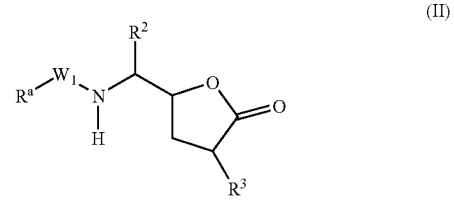

(II)

optionally with any hydroxy or amino groups protected, wherein R$^a$, R$^2$, R$^3$ and W$_1$ are as defined above, with a compound of formula R$^4$—NH$_2$, wherein R$^4$ is as defined above, and thereafter optionally as necessary deprotecting a compound of formula (I) which is protected;

(b) preparing a compound of formula (I) wherein W$_1$ represents CO which comprises reacting a compound of formula (III)

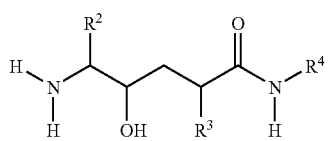

optionally with any hydroxy or amino groups protected, wherein $R^2$, $R^3$ and $R^4$ are as defined above, with a compound of formula $R^a$—COOH, or an activated and optionally protected derivative thereof, wherein $R^a$ is as defined above, and thereafter optionally as necessary deprotecting a compound of formula (I) which is protected; or (c) preparing a compound of formula (I) wherein $W_1$ represents $SO_2$ which comprises reacting a compound of formula (III)

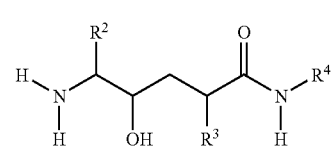

optionally with any hydroxy or amino groups protected, wherein $R^2$, $R^3$ and $R^4$ are as defined above, with a compound of formula (IV)

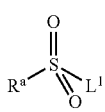

or an optionally protected derivative thereof, wherein $R^a$ is as defined above and $L^1$ represents a suitable leaving group, such as a halogen atom (eg. chlorine), and thereafter optionally as necessary deprotecting a compound of formula (I) which is protected; or (d) deprotecting a compound of formula (I) which is protected; or (e) interconversion of compounds of formula (I) to other compounds of formula (I).

Process (a) typically comprises heating a mixture of compounds of formula (II) and $R^4$—$NH_2$.

Process (b) is a conventional amide coupling reaction where the activated derivative may be, for example, the acid chloride, mixed anhydride, active ester or O-acyl-isourea. The reaction typically comprises mixing compounds of formula (III) and $R^a$—COOH with a suitable coupling agent (such as N-cyclohexylcarbodiimide-N'-methyl polystyrene in the presence of HOBT) in a suitable solvent (such as dimethylformamide or dichloromethane) at a suitable temperature e.g. room temperature.

Process (c) typically comprises the use of a suitable base, eg. N-methylmorpholine or polystyrene-N-methylmorpholine in the presence of catalytic (10%) dimethylaminopyridine (DMAP) in a suitable solvent eg. dimethylformamide and/or dichloromethane.

In process (d), examples of protecting groups and the means for their removal can be found in T. W. Greene and P. G. M. Wuts 'Protective Groups in Organic Synthesis' (J. Wiley and Sons, 3rd Ed. 1999). Suitable amine protecting groups include sulphonyl (e.g. tosyl), acyl (e.g. benzyloxycarbonyl or t-butoxycarbonyl) and arylalkyl (e.g. benzyl), which may be removed by hydrolysis or hydrogenolysis as appropriate. Other suitable amine protecting groups include trifluoroacetyl (—$COCF_3$) which may be removed by base catalysed hydrolysis. Suitable hydroxy protecting groups would be silyl based groups such as t-butyldimethylsilyl, which may be removed using standard methods, for example use of an acid such as trifluoroacetic or hydrochloric acid or a fluoride source such as tetra n-butylammonium fluoride.

Process (e) may be performed using conventional interconversion procedures such as epimerisation, oxidation, reduction, alkylation, nucleophilic aromatic substitution, ester hydrolysis, amide bond formation, t-butoxycarbonyl group addition or removal and sulphonylation.

Compounds of formula (II) where $W_1$ represents CO may be prepared in accordance with the following procedure:

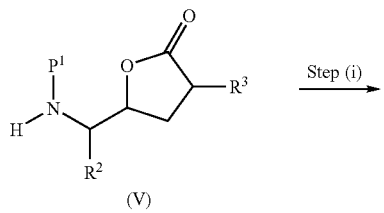

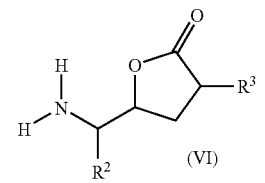

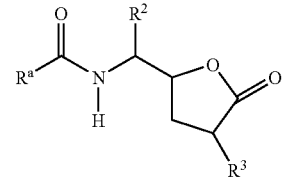

$R^a$, $R^2$ and $R^3$ are as defined above and $P^1$ represents a suitable protecting group such as t-butoxycarbonyl.

Step (i) typically comprises mixing a compound of formula (V) with a suitable acid (such as trifluoroacetic acid) in a suitable solvent (such as dichloromethane) at a suitable temperature e.g. room temperature.

Step (ii) typically comprises mixing compounds of formula (VI) and $R^a$—COOH with a suitable coupling agent (such as N-cyclohexylcarbodiimide-N'-methyl polystyrene in the presence of HOBT) in a suitable solvent (such as dimethylformamide or dichloromethane) at a suitable temperature e.g. room temperature.

Compounds of formula (II) where $W_1$ represents $SO_2$ may be prepared in an identical manner to the process described above for preparing compounds of formula (I) where $W_1$ represents CO, with the exception that in step (ii), a compound of formula (IVb) as defined above is used in place of a compound of formula R$^a$—COOH and that the conditions of process (c) described above are used in place of those described for step (ii).

Compounds of formula (III) may be prepared in accordance with the following procedure:

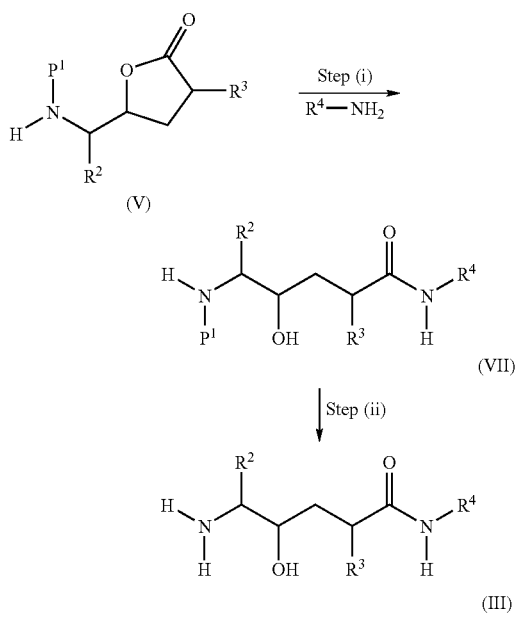

wherein R$^2$, R$^3$, R$^4$ are as defined above and P$^1$ represents a suitable protecting group such as t-butoxycarbonyl.

Step (i) typically comprises heating a compound of formula (V) in neat amine R$^4$—NH$_2$ to a suitable temperature e.g. 60° C.

Step (ii) typically comprises mixing a compound of formula (VII) with a suitable acid (such as trifluoroacetic acid) in a suitable solvent (such as dichloromethane) at a suitable temperature e.g. room temperature.

Compounds of formula (IV) are either known and/or may be obtained commercially and/or may be prepared in accordance with known procedures.

Compounds of formula (V) may be prepared in accordance with the synthesis described in Journal of Organic Chemistry (1986) 51(21), 3921.

As a further aspect of the invention there is thus provided a compound of formula (I) or a pharmaceutically acceptable salt or solvate thereof for use as a pharmaceutical, particularly in the treatment of patients with diseases characterised by elevated β-amyloid levels or β-amyloid deposits.

According to another aspect of the invention, there is provided the use of a compound of formula (I) or a physiologically acceptable salt or solvate thereof for the manufacture of a medicament for the treatment of patients with diseases characterised by elevated β-amyloid levels or β-amyloid deposits.

In a further or alternative aspect there is provided a method for the treatment of a human or animal subject with diseases characterised by elevated β-amyloid levels or β-amyloid deposits, which method comprises administering to said human or animal subject an effective amount of a compound of formula (I) or a physiologically acceptable salt or solvate thereof.

As a further aspect of the invention there is thus provided a pharmaceutical composition comprising a compound of formula (I) or a pharmaceutically acceptable salt or solvate thereof for use in the treatment of diseases characterised by elevated β-amyloid levels or β-amyloid deposits.

It will be appreciated by those skilled in the art that reference herein to treatment extends to prophylaxis as well as the treatment of diseases characterised by elevated β-amyloid levels or β-amyloid deposits.

The compounds according to the invention may be formulated for administration in any convenient way, and the invention therefore also includes within its scope pharmaceutical compositions for use in the therapy of diseases characterised by elevated β-amyloid levels or β-amyloid deposits, comprising a compound of formula (I) or a physiologically acceptable salt or solvate thereof together, if desirable, with one or more physiologically acceptable diluents or carriers.

It will be appreciated that diseases characterised by elevated β-amyloid levels or β-amyloid deposits include Alzheimer's disease, mild cognitive impairment, Down's syndrome, hereditary cerebral haemorrhage with β-amyloidosis of the Dutch type, cerebral β-amyloid angiopathy and various types of degenerative dementias, such as those associated with Parkinson's disease, progressive supranuclear palsy, cortical basal degeneration and diffuse Lewis body type of Alzheimer's disease.

Most preferably, the disease characterised by elevated β-amyloid levels or β-amyloid deposits is Alzheimer's disease.

There is also provided a process for preparing such a pharmaceutical formulation which comprises mixing the ingredients.

The compounds according to the invention may, for example, be formulated for oral, inhaled, intranasal, buccal, enteral, parenteral, topical, sublingual, intrathecal or rectal administration, preferably for oral administration.

Tablets and capsules for oral administration may contain conventional excipients such as binding agents, for example syrup, acacia, gelatin, sorbitol, tragacanth, mucilage of starch, cellulose or polyvinyl pyrrolidone; fillers, for example, lactose, microcrystalline cellulose, sugar, maize-starch, calcium phosphate or sorbitol; lubricants, for example, magnesium stearate, stearic acid, talc, polyethylene glycol or silica; disintegrants, for example, potato starch, croscarmellose sodium or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxymethyl cellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example almond oil, fractionated coconut oil, oily esters, propylene glycol or ethyl alcohol; or preservatives, for example, methyl or propyl p-hydroxybenzoates or sorbic acid. The preparations may also contain buffer salts, flavouring, colouring and/or sweetening agents (e.g. mannitol) as appropriate.

For buccal administration the compositions may take the form of tablets or lozenges formulated in conventional manner.

The compounds may also be formulated as suppositories, e.g. containing conventional suppository bases such as cocoa butter or other glycerides.

The compounds according to the invention may also be formulated for parenteral administration by bolus injection or continuous infusion and may be presented in unit dose form, for instance as ampoules, vials, small volume infusions or pre-filled syringes, or in multi-dose containers with an added preservative. The compositions may take such forms as solutions, suspensions, or emulsions in aqueous or non-aqueous vehicles, and may contain formulatory agents such as anti-oxidants, buffers, antimicrobial agents and/or tonicity adjusting agents. Alternatively, the active ingredient may be in powder form for constitution with a suitable vehicle, e.g. sterile, pyrogen-free water, before use. The dry solid presentation may be prepared by filling a sterile powder aseptically into individual sterile containers or by filling a sterile solution aseptically into each container and freeze-drying.

When the compounds of the invention are administered topically they may be presented as a cream, ointment or patch.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 0.05 to 20 mg, for example 0.2 to 5 mg; and such unit doses may be administered more than once a day, for example one, two, three or four times per day (preferably once or twice), so that the total daily dosage is in the range of about 0.5 to 100 mg; and such therapy may extend for a number of weeks or months.

All publications, including but not limited to patents and patent applications, cited in this specification are herein incorporated by reference as if each individual publication were specifically and individually indicated to be incorporated by reference herein as though fully set forth.

EXAMPLES

Description 1

[(1S,2S,4R)1-Benzyl-4-(3,3-dimethylbutylcarbamoyl)-2-hydroxypentyl]-carbamic acid t-butyl ester (D1)

[(S)-1-(4-Methyl-5-oxo-tetrahydrofuran-2-yl)-2-phenyl-ethyl]-carbamic acid t-butyl ester (synthesis described in Journal of Organic Chemistry (1986) 51(21), 3921) (245 mg, 0.77 mmol) was treated with 3,3-dimethyl butylamine (1.0 g, 9.9 mmol) and the resulting solution was heated at 70° C. for 24 h. The solution was then evaporated to dryness and the residue was partitioned between 1M hydrochloric acid and ethyl acetate. The organic phase was separated and washed with further 1M hydrochloric acid and brine. It was then dried over MgSO$_4$, filtered and evaporated to afford the crude product as a white foam (303 mg). Purification by chromatography on silica eluting with 0–2% methanol in dichloromethane gave the title compound (D) (264 mg, 82%).

MS (ES) MNa$^+$=443 $^1$H NMR (400 MHz, CDCl$_3$) 0.92 (9H, s), 1.10 (3H, d, J 7.2 Hz), 1.30–1.43 (11H, m), 1.57–1.75 (2H, m), 2.50 (1H, m), 2.90 (2H, m), 3.24 (2H, m), 3.66 (2H, m), 3.80 (1H, d, J4.4 Hz), 4.85 (1H, br.d), 5.68 (1H, br.s) and 7.15–7.30 (5H, m).

Description 2

(2R,4S,5S)-5-Amino hydroxy-2-methyl-6-phenyl-hexanoic acid (3,3-dimethylbutyl)-amide (D2)

[(1S,2S,4R)-1-Benzyl-4-(3,3-dimethylbutylcarbamoyl)-2-hydroxypentyl]-carbamic acid t-butyl ester (D1) (264 mg, 0.63 mmol) was treated with 4M HCl in dioxane (5 ml) and the resulting solution was stirred at room temperature for 1 h. It was then evaporated to dryness and the residue was partitioned between satd. aq. sodium carbonate and ethyl acetate. The aqueous layer was separated and extracted with further ethyl acetate. The combined organic extracts were washed with brine, dried over MgSO$_4$, filtered and evaporated to afford the amine (D2). (179 mg, 89%).

MS (ES) MH$^+$=321 $^1$H NMR (400 MHz, CDCl$_3$) 0.93 (9H, s), 1.18 (3H, d, J 7.0 Hz), 1.40 (2H, t, J 8.5 Hz), 1.48 (1H, m), 1.60–1.90 (3H, br.s), 1.88 (1H, m), 2.48 (1H, dd, J 9.5, 14.0 Hz), 2.59 (1H, m), 2.82 (1H, m), 2.94 (1H, dd, J 4.0, 14.0 Hz), 3.20–3.37 (3H, m), 5.81 (1H, br.s.) and 7.13–7.33 (5H, m).

Description 3

(2R,4S,5S)-5-t-Butoxycarbonylamino-4-hydroxy-2-methyl-6-phenylhexanoic acid (bicyclo[2.2.1]hept-2-yl)amide (D3)

[(S)-1-(4-Methyl-5-oxo-tetrahydrofuran-2-yl)-2-phenyl-ethyl]-carbamic acid t-butyl ester (synthesis described in Journal of Organic Chemistry (1986) 51(21), 3921) (22.2 g) was treated with (±)exo-norbornylamine (62.8 g) and the resulting mixture was heated at 70° C. overnight. The mixture was allowed to cool and poured into HCl aq. (1M; 700 ml) and extracted twice with ethyl acetate. The combined organic layers were washed with sodium bicarbonate solution, water and brine, dried and evaporated to a gummy solid. Ether was added and the mixture was stirred and then left to stand overnight. The resulting white solid precipitate was collected by filtration and dried to give D3 (14 g).

Description 4

(2R,4S,5S)-5-Amino-4-hydroxy-2-methyl-6-phenyl-hexanoic acid (bicyclo[2.2.1]hept-2-yl)amide (D4)

(2R,4S,5S)-5-t-Butoxycarbonylamino-4-hydroxy-2-methyl-6-phenylhexanoic acid (bicyclo[2.2.1]hept-2-yl)amide (D3) (14 g) was dissolved in a solution of HCl in dioxan (4M; 220 ml) and stirred at room temperature for 2.5 h. The solution was evaporated to dryness and the residue was triturated with ether to give a white solid HCl salt. To this was added ethyl acetate and sodium bicarbonate solution and a dense white solid began to precipitate almost immediately. This was collected and dried at 40° C. in vacuo over KOH. The wet solid was dried to give D4 as a white brittle foam (8.75 g).

MS (ES) MH$^+$=331

Description 5

{(S)-1-[(2S,4R)-4-(3-Methyl-but-2-enyl)-5-oxo-tetrahydro-furan-2-yl]-2-phenyl-ethyl}-carbamic acid tert-butyl ester (D5)

Prepared analogously to the synthesis of [(S)-1-(4-methyl-5-oxo-tetrahydrofuran-2-yl)-2-phenylethyl]-carbamic acid t-butyl ester in Journal of Organic Chemistry (1986) 51(21), 3921, using 4-bromo-2-methyl-2-butene in place of methyl iodide, to afford D5 in 84% yield.

$^1$H NMR (400 MHz, CDCl$_3$); 1.38 (9H, s), 1.59 (3H, s), 1.67 (3H, s), 1.92 (1H, m), 2.25 (2H, m), 2.41 (1H, m), 2.69 (1H, m), 2.89 (2H, m), 3.99 (1H,m), 4.44 (1H, m), 4.53 (1H, d J 9.7 Hz), 5.03 (1H, m) and 7.22–7.33 (5H,m).

Description 6

[(1S,2S,4R)-1-Benzyl-4-(bicyclo[2.2.1]hept-2-ylcarbamoyl)-2-hydroxy-7-methyl-oct-6-enyl]-carbamic acid tert-butyl ester (D6)

{(S)-1-[(2S,4R)-4-(3-Methyl-but-2-enyl)-5-oxo-tetrahydro-furan-2-yl]-2-phenyl-ethyl}-carbamic acid tert-butyl ester (D5) was treated with (±)exo-norbornylamine as described in D3 to afford D6 as a white solid (60%).

MS (ES) MH$^+$=485, M–H$^-$=483.

Description 7

[(1S,2S,4R)-1-Benzyl-4-(bicyclo [2.2.1]hept-2-ylcarbamoyl)-2-hydroxy-7-methyl-octyl]-carbamic acid tert-butyl ester (D7)

[(1S,2S,4R)-1-Benzyl-4-(bicyclo[2.2.1]hept-2-ylcarbamoyl)-2-hydroxy-7-methyl-oct-6-enyl]-carbamic acid tert-butyl ester (D6) (1.61 g, 3.33 mmol) in methanol (30 ml) was hydrogenated over 10% Pd/C (300 mg) for 3.75 h. The catalyst was filtered and the filtrate evaporated to afford D7 (93%).

MS (ES) MH$^+$=487, M–H$^-$=485.

Description 8

(2R,4S,5S)-5-Amino-4-hydroxy-2-(3-methyl-butyl)-6-phenyl-hexanoic acid bicyclo[2.2.1]hept-2-ylamide (D8)

D8 was prepared from D7 by the method described in D4, as a white foam (100%).

MS (ES) MH$^+$=387, M–H$^-$=385.

Description 9

(2R,4S,5S)-5-t-Butoxycarbonylamino-4-hydroxy-2-methyl-6-phenylhexanoic acid cyclohexylamide (D9)

Prepared in an analogous manner to D3 using cyclohexylamine instead of (±)exo-norbornylamine.

Description 10

(2R,4S,5S)-5-Amino-4-hydroxy-2-methyl-6-phenyl-hexanoic acid cyclohexylamide (D10)

(2R,4S,5S)-5-t-Butoxycarbonylamino-4-hydroxy-2-methyl-6-phenylhexanoic acid cyclohexylamide (D9) (9.43 g) was deprotected in an analogous fashion to D4 to give D10 as a white solid (2 crops, 5.53 g).

MS (ES) MH$^+$=319

Description 11

3-Methylsulfonyl-5-nitrobenzoic acid (D11)

A solution of 3-methylsulfonylbenzoic acid (16.3 g) in 20% oleum (100 ml) was cooled (ice-bath) and fuming nitric acid (>90%; 90 ml) was added dropwise. The resulting mixture was stirred for 4 days at room temperature and was then poured onto crushed ice. The acids were partially neutralised by addition of solid sodium bicarbonate (to ~pH2). The solid precipitate was filtered off and dried to give, as a pale beige solid D11 (15.6 g).

$^1$H NMR (DMSO-d$_6$) 3.44 (3H, s), 8.75 (1H, t, J=1.5 Hz), 8.84 (1H, t, J=1.8 Hz), 8.86 (1H, t, J=1.9 Hz), 14.20 (1H, v. br. s).

Description 12

3-Amino-5-methylsulphonylbenzoic acid (D12)

3-Methylsulfonyl-5-nitrobenzoic acid (D11) (7.5 g) was dissolved in methanol (250 ml) and Raney nickel was added. The mixture was stirred under hydrogen at atmospheric pressure and room temperature overnight. The mixture was heated to dissolve precipitated product and filtered hot. The filter cake was washed with hot MeOH and the combined filtrates were evaporated to give D12 (5.97 g) an off-white solid.

$^1$H NMR (DMSO-d$_6$) 3.16 (3H, s), 5.95 (2H, br. s), 7.24 (1H, m), 7.43 (1H, m), 7.49 (1H, m).

Description 13

3-Hydroxy-5-methylsulfonylbenzoic acid (D13)

3-Amino-5-methylsulphonylbenzoic acid (D12) (7.24 g) was dissolved in a mixture of conc H$_2$SO$_4$ (100 ml) and water (300 ml) and cooled to 5° C. sodium nitrite (5.1 g) in water (15 ml) was added dropwise and the mixture was thereafter stirred in the cooling bath for 15 min and with the cooling bath removed for 40 min. It was then heated at 90° C. for 1 h. The heating was removed and the reaction was allowed to stand overnight. The mixture was partially neutralised (~pH1) with solid sodium bicarbonate until a solid precipitate formed. The mixture was extracted 3 times with ethyl acetate and the combined extracts were washed with water and brine, dried (Mg SO$_4$) and evaporated to a solid which was triturated with ether to give D13 (2 crops, 4.12 g).

$^1$H NMR (DMSO-d$_6$) 3.24 (3H, s), 7.48 (1H, m), 7.61 (1H, m), 7.84 (1H, m), 10.64 (1H, br. s), 13.42 (1H, v. br. s).

Description 14

Methyl 3-methoxy-5-methylsuLfonylbenzoate (D14)

3-Hydroxy-5-methylsulfonylbenzoic acid (D13) was dissolved in DMF (42 ml) and treated with caesium carbonate (14.1 g) and methyl iodide (8.6 ml) The mixture was sonicated under argon for 45 min. and stirred for 3 h at room temperature. The DMF was evaporated in vacuo and the residue was partitioned between ethyl acetate and 2M hydrochloric acid. The aqueous layer was re-extracted twice with ethyl acetate and the combined extracts were washed with sodium bicarbonate solution, sodium thiosulfate solution, water and brine, dried (Mg SO$_4$) and evaporated to a semi solid. Trituration with ether gave D14 (2 crops, 2.94 g).

¹H NMR (DMSO-d₆) 3.30 (3H, s), 3.91 (3H, s), 3.93 (3H, s), 7.72 (1H, m), 7.74 (1H, m), 8.00 (1H, m).

Description 15

3-Methoxy-5-methylsulfonylbenzoic acid (D15)

Methyl 3-methoxy-5-methylsulfonylbenzoate (D14) (2.94 g) was dissolved in dioxan (18 ml) and lithium hydroxide monohydrate (0.762 g) in water (18 ml) was added. The mixture was stirred at room temperature for 2 h and then sufficient Amberlyst-15 H⁺ resin was added to adjust the pH to ~4. The resin was removed by filtration and washed well with dioxan and the combined filtrates were evaporated. The residue was triturated with ether to give D15 as a pale buff solid (2 crops, 2.29 g).
¹H NMR (DMSO-d₆) 3.29 (3H, s), 3.92 (3H, s), 7.68 (1H, m), 7.72 (1H, m), 7.98 (1H, m), 13.52 (1H, v. br. s).

Description 16

Methyl 3-amino-5-methylsulphonyl benzoate (D16)

3-Amino-5-methylsulphonyl benzoic acid (D12) (1.0 g) was dissolved in methanol (100 ml) and HCl gas was passed in. The mixture was refluxed for 45 min. and the MeOH was evaporated. Sodium bicarbonate solution was added to give pH ~9 and the mixture was extracted twice with ethyl acetate. The combined extracts were washed with water and brine, dried (MgSO₄) and evaporated to give D16 as an off-white solid.
¹H NMR (DMSO-d₆) 3.17 (3H, s), 3.86 (3H, s), 6.04 (2H, s), 7.28 (1H, m), 7.45 (1H, m), 7.50 (1H, m).

Description 17

Methyl 3-(4-bromobutyramido)-5-methylsulfonyl benzoate (D17)

Methyl 3-amino-5-methylsulphonyl benzoate (D16) (0.856 g) was dissolved in dichloromethane (50 ml) and pyridine (2.6 ml). 4-Bromobutyryl chloride (0.73 mL) was added by syringe and the mixture was stirred for 2 h. The solution was washed with 10% aqueous citric acid, sodium bicarbonate solution and brine, dried (MgSO₄) and evaporated to a solid. This was triturated with ether to give D17 as an off-white solid (1.25 g).
¹H NMR (DMSO-d₆) 2.14 (2H, quintet, J=6.9 Hz), 2.55 (2H, t, J=7.2 Hz), 3.26 (3H, s), 3.61 (2H, t, J=6.6 Hz), 3.90 (3H, s), 8.08 (1H, m), 8.46 (1H, m), 8.51 (1H, m), 10.62 (1H, s).

Description 18

Methyl 3-methylsulfonyl-5-(2-oxopyrrolidin-1-yl)-benzoate (D18)

Methyl 3-(4-bromobutyramido)-5-methyl sulfonyl benzoate (D17) (1.0 g) was dissolved in dioxan (25 ml) and DBU (0.65 ml) was added. Initially a clear solution was obtained but the hydrobromide of DBU soon began to precipitate. The mixture was stirred for 1 h at room temperature and then poured into 10% aqueous citric acid and extracted twice with ethyl acetate. The combined extracts were washed with sodium bicarbonate solution, water and brine, dried (MgSO₄) and evaporated to a solid residue which was triturated with ether to give D18 as a pale yellow solid (0.72 g).

¹H NMR (DMSO-d₆) 2.11 (2H, quintet, J=7.5 Hz), 2.57 (2H, t, J=8.0 Hz), 3.30 (3H, s), 3.93 (3H, s), 3.96 (2H, t, J=7.0 Hz), 8.15 (1H, m), 8.40 (1H, m), 8.58 (1H, m).

Description 19

3-Methylsulfonyl-5-(2-oxopyrrolidin-1-yl)benzoic acid (D19)

Methyl 3-methylsulfonyl-5-(2-oxopyrrolidin-1-yl)-benzoate (D18) (0.717 g) was suspended in dioxan (3.6 ml) and treated with a solution of lithium hydroxide monohydrate (0.153 g) in water (3.6 ml). The mixture was stirred for 2 h at room temperature and a clear solution was formed. The pH was adjusted to ~4 by addition of Amberlyst-15 H⁺ resin. The resin was removed by filtration and washed well with dioxan. The combined filtrates were evaporated and the residue dried. Trituration with ether gave D19 (0.51 g) as a pale cream solid.
¹H NMR (DMSO-d₆) 2.11 (2H, quintet, J=7.5 Hz), 2.57 (1H, t, J=8.0 Hz), 3.29 (3H, s), 3.96 (2H, t, J=7.0 Hz), 8.14 (1H, m), 8.41 (1H, m), 8.53 (1H, m).

Description 20 t-Butyl 2-chloro-6-methoxypyridine-4-carboxylate (D20)

2-Chloro-6-methoxypyridine-4-carboxylic acid (3.96 g) was heated in thionyl chloride (40 ml) at reflux for 2 h. The excess thionyl chloride was evaporated in vacuo and the residue was re-evaporated twice with dichloromethane to give the acid chloride as an almost colourless oil (4.17 g). This was dissolved in THF (20 ml) and cooled (ice-bath). Potassium t-butoxide (2.72 g) was added. The mixture darkened and a vigorous reaction took place. Further potassium t-butoxide (1.0 g) was added and the mixture was allowed to stir at room temperature for 48 hr. The mixture was then partitioned between ethyl acetate and 10% aq. citric acid. The aqueous layer was re-extracted and the combined extracts were washed with aq. bicarbonate, water and brine, dried (MgSO₄) and evaporated to a semi solid which was chromatographed on silica eluting with hexane/ether. The product was obtained as a colourless solid after crystallisation from hexane; and a second clean crop was obtained by recrystallisation of the material from the mother-liquors from ethanol. The total yield of D20 was 1.53 g
¹H NMR (DMSO-d₆) 1.54 (9H, s), 3.90 (3H, s), 7.16 (1H, d, J=1 Hz), 7.37 (1H, d, J=1 Hz).

Description 21 t-Butyl 6-methoxy-2-methylthiopyridine-4-carboxylate (D21)

t-Butyl 2-chloro-6-methoxypyridine-4-carboxylate (D20) (0.72 g) was heated with sodium methanethiolate (0.414 g) in DMF (12 ml) at 60° C. for 50 min. The solution was poured into 10% aq. citric acid and extracted twice with ethyl acetate. The combined extracts were washed with aqueous sodium bicarbonate, water and brine, dried (MgSO₄) and evaporated to a yellow semi-solid which was chromatographed on silica, eluting with hexane/ethyl acetate, giving D21 (0.33 g).
¹H NMR (CDCl₃) 1.57 (9H, s), 2.58 (3H, s), 3.97 (3H, s), 6.91 (1H, d, J=1 Hz), 7.26 (1H, J=1 Hz).

Description 22 t-Butyl 6-methoxy-2-methyl-sulfonylpyridine-4-carboxylate (D22)

t-Butyl 6-methoxy-2-methylthiopyridine-4-carboxylate (D21) (0.33 g) was dissolved in dichloromethane (13 ml) and cooled (ice-bath). 3-Chloroperbenzoic acid (86%; 0.57 g) was added. The mixture was stirred with cooling for 1 h and then allowed to warm to room temp and stirred for a further 2 h. Ethyl acetate was added and the mixture was washed with 10% sodium carbonate solution (twice), sodium thiosulfate solution, water and brine, dried (MgSO$_4$) and evaporated to give D22 (0.33 g).

$^1$H NMR (CDCl$_3$) 1.60 (9H, s), 3.22 (3H, s), 4.04 (3H, s), 7.51 (1H, d, J=1 Hz), 8.10 (1H, d, J=1 Hz).

Description 23

2-Methoxy-6-methylsulfonylpyridine-4-carboxylic acid (D23)

t-Butyl 6-methoxy-2-methyl-sulfonylpyridine-4-carboxylate (D22) (0.33 g) was stirred at room temperature in a solution of HCl in dioxan (4M; 10 ml) for 20 h. The reaction mixture was evaporated to dryness and the residue was partitioned between 10% aq. sodium carbonate and ethyl acetate. The aqueous layer was washed twice with ethyl acetate and then acidified to ~pH4 by addition of solid citric acid. The solution was saturated with sodium chloride and extracted 3 times with ethyl acetate and the combined extracts were washed with water (3×10 mL), brine and dried (MgSO$_4$). Evaporation gave D23 as a pale yellow solid (0.213 g).

$^1$H NMR (CDCl$_3$+trace DMSO-d$_6$) 3.23 (3H, s), 4.05 (3H, s), 7.56 (1H, d, J=1 Hz), 8.16 (1H, d, J=1 Hz).

Description 24

(2R,4S,5S)-5-Amino-4-hydroxy-6-phenyl-2-prop-2-ynylhexanoic acid bicyclo [2.2.1]hept-2-ylamide (D24)

D24 was prepared in an analogous manner to the process described in D4 from [(1S,2S,4R)-1-benzyl-4-(bicyclo [2.2.1]hept-2-ylcarbamoyl)-2-hydroxyhept-6-ynyl]carbamic acid tert-butyl ester (obtained by an analogous manner to D6) to afford a white foam (96%).
MS (ES) M+H=355, M−H=353.

Example 1

N-[(1S,2S,4R)-1-Benzyl-4-(3,3-dimethylbutylcarbamoyl)-2-hydroxypentyl]-3-methanesulfonyl-benzamide (E1)

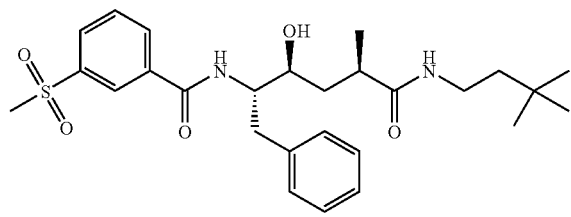

Solid Phase Method.

N-Cyclohexylcarbodiimide-N'-methyl polystyrene (100 mg @ 1.70 mmol/g; ex. Novabiochem) was treated with dichloromethane (0.5 ml) followed by a solution of 1-hydroxybenzotriazole (22 mg, 0.14 mmol) in 4:1 dichloromethane/DMF (0.5 ml). 3-Methanesulfonyl benzoic acid (28 mg, 0.14 mmol) in DMF (0.5 ml) and (2R,4S,5S)-5-amino-4-hydroxy-2-methyl-6-phenylhexanoic acid (3,3-dimethylbutyl)-amide (D2) (30 mg, 0.094 mmol) in dichloromethane (0.5 ml) were then added and the mixture was stirred gently overnight at room temperature. It was then diluted with dichloromethane (0.5 ml) and treated with methylisocyanate polystyrene (100 mg @ 1.80 mmol/g; ex. Novabiochem) and tris-(2-aminoethyl)-amine polystyrene (100 mg @ 3.20 mmol/g; ex. Novabiochem), and the mixture was stirred gently for a further 1.5 h. It was then filtered and the spent resins were washed with DMF (1 ml) and dichloromethane (1 ml). The combined filtrates were evaporated to dryness and the residue was triturated with diethyl ether/hexane to afford the title compound (E1) as a white solid (23 mg, 49%).

MS (ES) MH$^+$=503, M−H$^-$=501.

Solution Phase Method

To a solution of 3-methanesulfonyl benzoic acid (77 mg, 0.39 mmol) and 1-hydroxybenzotriazole (52 mg, 0.39 mmol) in 2:1 dichloromethane/DMF (3.0 ml) was added (2R,4S,5S)-5-amino-4-hydroxy-2-methyl-6-phenylhexanoic acid (3,3-dimethylbutyl)-amide (D2) (100 mg, 0.32 mmol) and 1-(3-dimethylaminopropyl)-3-ethylcarbodiimide hydrochloride (86 mg, 0.45 mmol). The resulting solution was stirred at room temperature overnight and then evaporated to dryness. The residue was partitioned between ethyl acetate and 1M hydrochloric acid. The organic phase was separated and washed with further 1M hydrochloric acid, dil. aq. NaHCO$_3$ and brine. It was dried over MgSO$_4$, filtered and evaporated to afford the crude product which was triturated with ether to afford the title compound (63 mg, 39%).

Example 2

N-[1S,2S,4R)-1-Benzyl-4-(bicyclo [2.2.1]hept-2-ylcarbamoyl)-2-hydroxyhept-6-ynyl]-3-methanesulfonylbenzamide (E2)

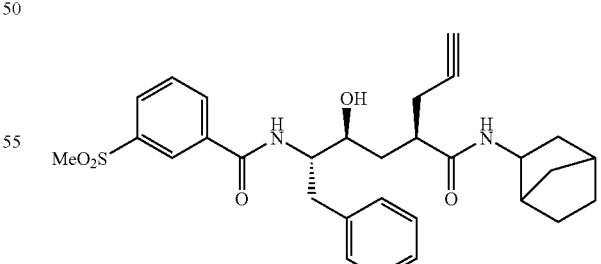

Prepared in an analogous manner to E1 from 3-methylsulfonylbenzoic acid and (2R,4S,S5)-5-amino-4-hydroxy-6-phenyl-2-prop-2-ynylhexanoic acid bicyclo[2.2.1]hept-2-ylamide (D24)
MS (ES) MH$^+$=537

Example 3

N-[(1S,2S,4R)-1-Benzyl-4-(bicyclo[2.2.1]hept-2-ylcarbamoyl)-2-hydroxypentyl]-3-methoxy-5-methylsulfonylbenzamide (E3)

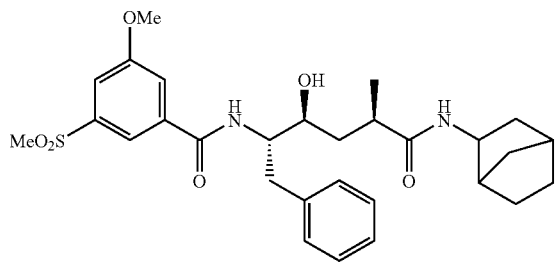

Prepared in an analogous manner to E1 from 3-methoxy-5-methylsulfonylbenzoic acid (D15) and (2R,4S,5S)-5-amino-4-hydroxy-2-methyl-6-phenylhexanoic acid (bicyclo[2.2.1]hept-2-yl)amide (D4).

MS (ES) MH$^+$=543

Example 4

N-[(1S,2S,4R)-1-Benzyl-4-(bicyclo[2.2.1]hept-2-ylcarbamoyl)-2-hydroxypentyl]-3-methylsulfonyl-5-n-propoxybenzamide (E4)

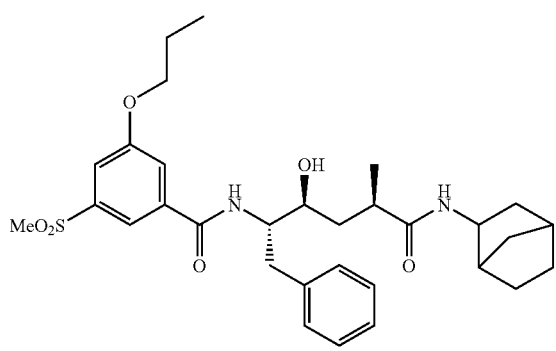

3-Hydroxy-5-methylsulfonylbenzoic acid (D13) (86 mg) and (2R,4S,5S)-5-amino-4-hydroxy-2-methyl-6-phenylhexanoic acid (bicyclo[2.2.1]hept-2-yl)amide (D4) (43 mg) were reacted as in E1 to give an off-white solid (93 mg). This material (92 mg) was treated with caesium carbonate (85 mg) and allyl bromide (45 µl) in DMF (1.86 ml). The reaction was sonicated for 0.5 h and stirred at room temp overnight. The mixture was poured into 2.0M HCl and extracted twice with ethyl acetate and the extracts were washed with sodium bicarbonate solution, water and brine, dried (MgSO$_4$) and evaporated. The crude material was chromatographed on silica, eluting with DCM/MeOH to give N-[(1S,2S,4R)-1-benzyl-4-(bicyclo[2.2.1]hept-2-ylcarbamoyl)-2-hydroxypentyl]-3-allyloxy-5-methylsulfonylbenzamide (55 mg). This compound (41 mg) was hydrogenated in MeOH (5 mL) with Pd—C(10%) catalyst (5 mg) at atmospheric pressure for 3 hr. The catalyst was filtered off and the filtrate was evaporated. The residue was chromatographed on silica, eluting with DCM/MeOH to give E4 (30 mg).

MS (ES) MH$^+$=571

Example 5

N-[(1S,2S,4R)-1-Benzyl-4-(bicyclo[2.2.1]hept-2-ylcarbamoyl)-2-hydroxy-7-methyl-octyl]-3-n-propoxy-5-methylsulfonyl benzamide (E5)

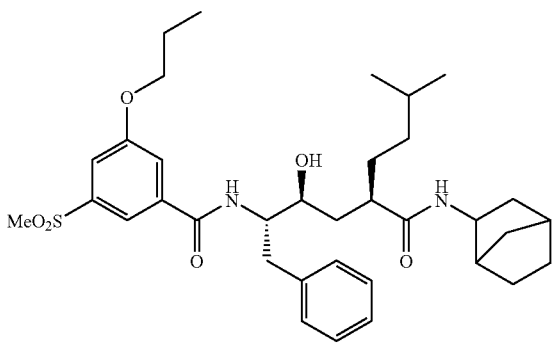

The title compound was prepared from (2R,4S,5S)-5-Amino-4-hydroxy-2-(3-methyl-butyl)-6-phenyl-hexanoic acid bicyclo[2.2.1]hept-2-ylamide (D8) (103 mg) and 3-hydroxy-5-methylsulfonylbenzoic acid (D13) (86 mg) in an analogous manner to the procedure described in E4.

MS (ES) MH$^+$=627

Example 6

N-[(1S,2S,4R)-1-Benzyl-4-cyclohexylcarbamoyl-2-hydroxypentyl]-3-methoxy-5-methylsulfonylpyridine-4-carboxamide (E6)

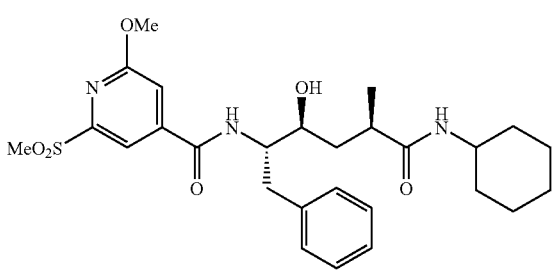

Prepared in an analogous manner to E1, from 2-methoxy-6-methylsulfonylpyridine-4-carboxylic acid (D23) and (2R,4S,5S)-5-amino-4-hydroxy-2-methyl-6-phenylhexanoic acid cyclohexylamide (D10).

MS (ES) MH$^+$=532

Example 7

N-[(1S,2S,4R)-1-Benzyl-4-(bicyclo[2.2.1]hept-2-ylcarbamoyl)-2-hydroxypentyl]3-methylsulfonyl-5-(2-oxopyrrolidin-1-yl)-benzamide (E7)

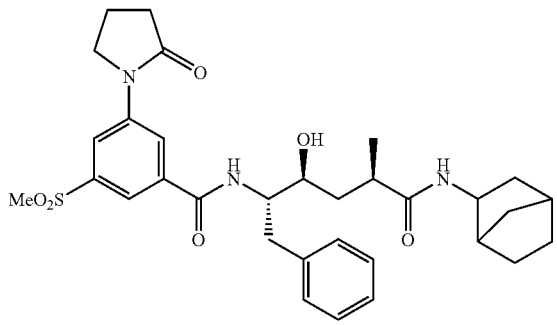

Prepared in an analogous manner to E1, from 3-methylsulfonyl-5-(2-oxopyrrolidin-1-yl)-benzoic acid (D19) and (2R,4S,5S)-5-Amino-4-hydroxy-2-methyl-6-phenylhexanoic acid (bicyclo[2.2.1]hept-2-yl)amide (D4).
MS (ES) MH$^+$=596

Example 8

N-[(1S,2S,4R)-1-Benzyl(bicyclo[2.2.1]hept-2-ylcarbamoyl)-2-hydroxypentyl]-3-methoxy-5-methylsulfonylpyridine-4-carboxamide (E8)

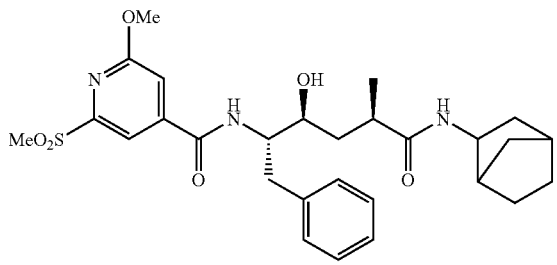

Prepared in an analogous manner to E1, from 2-Methoxy-6-methylsulfonylpyridine-4-carboxylic acid (D23) and (2R,4S,5S)-5-Amino-4-hydroxy-2-methyl-6-phenylhexanoic acid (bicyclo[2.2.1]hept-2-yl)amide (D4).
MS (ES) MH$^+$=544

Example 9

5-Methanesulfonyl-thiophene-2-carboxylic acid [(1S,2S,4R)-1-benzyl-4-(3,3-dimethyl-butylcarbamoyl)-2-hydroxypentyl]-amide (E9)

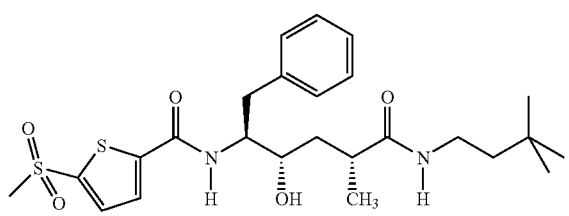

N-Cyclohexylcarbodiimide-N'-methyl polystyrene (138 mg @ 1.70 mmol/g; ex. Novabiochem) was treated with dichloromethane (0.5 ml) followed by a solution of 1-hydroxybenzotriazole (32 mg, 0.24 mmol) in 4:1 dichloromethane/DMF (0.5 ml). 5-Methanesulfonyl thiophene-2-carboxylic acid (50 mg, 0.23 mmol) in DMF (0.5 ml) and (2R,4S,5S)-5-amino-4-hydroxy-2-methyl-6-phenyl-hexanoic acid (3,3-dimethylbutyl)-amide (D2) (50 mg, 0.16 mmol) in dichloromethane (0.5 ml) were then added and the mixture was stirred gently overnight at room temperature. It was then diluted with dichloromethane (1 ml) and treated with methylisocyanate polystyrene (150 mg @ 1.80 mmol/g; ex. Novabiochem) and tris-(2-aminoethyl)-amine polystyrene (150 mg @ 3.20 mmol/g; ex. Novabiochem), and the mixture was stirred gently for a further 2 h. It was then filtered and the spent resins were washed with DMF (1 ml) and dichloromethane (1 ml). The combined filtrates were evaporated to dryness and the residue was triturated with diethyl ether to afford the title compound as a white solid (57 mg, 72%).
MS (ES) MH$^+$=509, M–H$^-$=507.

| Abbreviations | |
|---|---|
| DMF | dimethylformamide |
| DBU | diazabicycloundecane |
| DMSO | dimethylsulfoxide |
| THF | tetrahydrofuran |
| DCM | dichloromethane |
| FAM | carboxyfluorescein |
| TAMRA | carboxytetramethylrhodamine |
| [ ] | single amino acid letter code relating to peptide sequence |

Compounds of the invention may be tested for in vitro biological activity in accordance with the following assays:

(I) Asp-2 Inhibitory Assay

For each compound being assayed, in a 384 well plate, is added:— a) 1 µl of a DMSO solution of the test compound (IC$_{50}$ curve uses ten 1 in 2 serial dilutions from 500 µM)

b) 10 µl of substrate (FAM-[SEVNLDAEFK]-TAMRA) solution in buffer. This is prepared by diluting 2 ml of a 2 mM DMSO solution of the substrate into 400 ml of buffer (100 mM Sodium acetate pH=4.5, 1 1 Milli-Q water, 0.06% Triton X-100 (0.5 ml/l), pH adjusted to 4.5 using glacial acetic acid). Aminomethyl fluorescein (FAM) and tetramethyl rhodamine (TAMRA) are fluorescent molecules which co-operate to emit fluorescence at 535 nm upon cleavage of the SEVNLDAEFK peptide.

c) 10 µl enzyme solution. This is prepared by diluting 16 ml of a 500 nM enzyme solution into 384 ml of buffer (prepared as above).

Blank wells (enzyme solution replaced by buffer) are included as controls on each plate. Wells are incubated for 1 h at room temperature and fluorescence read using a Tecan Ultra Fluorimeter/Spectrophotometer (485 nm excitation, 535 nm emission).

(II) Asps-1 Inhibitory Assay

For each compound being assayed, in a 384 well plate, is added:— a) 1 µl of a DMSO solution of the test compound (IC$_{50}$ curve uses ten 1 in 2 serial dilutions from 500 µM).

b) 10 µl of substrate (FAM-[SEVNLDAEFK]-TAMRA) solution in buffer. This is prepared by diluting 2 ml of a 2 mM DMSO solution of the substrate into 400 ml of buffer (100 mM Sodium acetate pH=4.5, 1 1 Milli-Q water, 0.06% Triton X-100 (0.5 ml/l), pH adjusted to 4.5 using glacial acetic acid).

c) 10 μl enzyme solution. This is prepared by diluting 4 ml of a 6.3 μM enzyme solution into 496 ml of buffer (100 mM Sodium acetate pH=4.5, 40 mM sodium chloride, 900 ml Milli-Q water, 100 ml glycerol, 0.2% CHAPS (2 g/l), pH adjusted to 4.5 using glacial acetic acid).

Blank wells (enzyme solution replaced by buffer) are included as controls on each plate. Wells are incubated for 2 h at room temperature and fluorescence read using a Tecan Ultra Fluorimeter/Spectrophotometer (485 nm excitation, 535 nm emission).

(III) Cathepsin D Inhibitory Assay

For each compound being assayed, in a 384 well plate, is added:— a) 1 μl of a DMSO solution of the test compound ($IC_{50}$ curve uses ten 1 in 2 serial dilutions from 500 μM).
b) 10 μl of substrate (FAM-[SEVNLDAEFK]-TAMRA) solution in buffer. This is prepared by diluting 2 ml of a 2 mM DMSO solution of the substrate into 400 ml of buffer (100 mM Sodium acetate pH=4.5, 1 l Milli-Q water, 0.06% Triton X-100 (0.5 ml/l), pH adjusted to 4.5 using glacial acetic acid).
c) 10 μl enzyme solution. This is prepared by diluting 1.6 ml of a 200 unit/ml (in 10 mM HCl) enzyme solution into 398.4 ml of buffer (prepared as above).

Blank wells (enzyme solution replaced by buffer) are included as controls on each plate. Wells are incubated for 1 h at room temperature and fluorescence read using a Tecan Ultra Fluorimeter/Spectrophotometer (485 nm excitation, 535 nm emission).

Pharmacological Data

The compounds of E1 and E2 were tested in Assays (I) and (II) and the following data was obtained:

| Example | Asp-2 $IC_{50}$ (nM) | Asp-1 $IC_{50}$ (nM) |
| --- | --- | --- |
| E1 | 400 | 7700 |
| E2 | 330 | 5570 |

The compounds of E3–E8 were tested in Assays (I), (II) and (III) and the results for all Examples fell within the following ranges of inhibition: 10–160 nm (Asp-2), 10–200 nM (Asp-1) and 10–2700 nM (CatD).

The compound of E9 was tested in Assays (I), (II) and (III) and obtained the following inhibition: 180 nM (Asp-2), 3300 nM (Asp-1) and 9600 nM (CatD).

The invention claimed is:

1. A compound of formula (I):

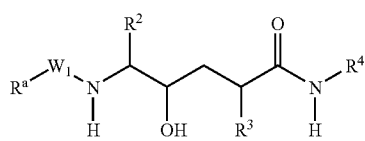

wherein $R^a$ represents a group of formula (a):

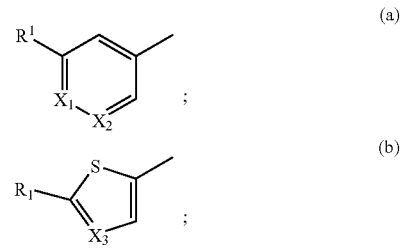

or a group of formula (b):

$R^1$ represents —$SO_2R^5$;
$R^5$ represents methyl or ethyl;
$X_1$ represents N, —C(—$R^6$)— or —C(—O—$R^7$)—;
$X_2$ and $X_3$ independently represent N, —C(—$R^8$)— or —C(—Y—$R^9$)—;
Y represents a bond, $CH_2$, O, S, CO, $NR^{10}$, —N($R^{10}$)C(O)—, —C(O)N($R^{10}$)—, COO, aryl, heterocyclyl or heteroaryl;
$R^6$ represents hydrogen, halogen, —$C_{1-6}$ alkyl, —$C_{2-6}$ alkenyl, —$C_{3-8}$cycloalkyl, —$C_{1-2}$ alkyl-$C_{3-8}$ cycloalkyl, heteroaryl, heterocyclyl or aryl;
$R^8$ represents halogen;
$R^7$, $R^9$ and $R^{10}$ independently represent hydrogen, —$C_{1-6}$ alkyl, —$C_{2-6}$ alkenyl, —$C_{3-8}$ cycloalkyl, —$C_{1-2}$ alkyl-$C_{3-8}$ cycloalkyl, heteroaryl, heterocyclyl or aryl;
$W_1$ represents CO or $SO_2$;
$R^2$ represents —$C_{5-8}$ alkyl, —$C_{1-6}$ alkyl-aryl, —$C_{1-6}$ alkyl-heteroaryl, —$C_{1-6}$ alkyl-heterocyclyl, —$C_{1-6}$ alkyl-$C_{3-8}$ cycloalkyl, —$C_{1-6}$ alkyl-S-aryl, —$C_{1-6}$ alkyl-O-aryl, —$C_{1-6}$ alkyl-S-heteroaryl or —$C_{1-6}$ alkyl-O-heteroaryl;
$R^3$ represents —$C_{1-6}$ alkyl or propargyl;
$R^4$ represents —$C_{1-6}$ alkyl, —$C_{1-6}$ alkyl-aryl, —$C_{1-6}$ alkyl-heteroaryl, —$C_{1-6}$ alkyl-heterocyclyl, —$C_{3-8}$ cycloalkyl, —$C_{1-6}$ alkyl-$C_{3-8}$ cycloalkyl or propargyl;
or a pharmaceutically acceptable salt.

2. A compound according to claim 1 which is
N-[(1S,2S,4R)-1-Benzyl-4-(3,3-dimethylbutylcarbamoyl)-2-hydroxypentyl]-3-methanesulfonyl-benzamide;
N-[1S,2S,4R)-1-Benzyl-4-(bicyclo[2.2.1]hept-2-ylcarbamoyl)-2-hydroxyhept-6-ynyl]-3-methanesulfonyl-benzamide;
N-[(1S,2S,4R)-1-Benzyl-4-(bicyclo[2.2.1]hept-2-ylcarbamoyl)-2-hydroxypentyl]-3-methoxy-5-methylsulfonylbenzamide;
N-[(1S,2S,4R)-1-Benzyl-4-(bicyclo[2.2.1]hept-2-ylcarbamoyl)-2-hydroxypentyl]-3-methylsulfonyl-5-n-propoxybenzamide;
N-[(1S,2S,4R)-1-Benzyl-4-(bicyclo[2.2.1]hept-2-ylcarbamoyl)-2-hydroxy-7-methyl-octyl]-3-n-propoxy-5-methyl sulfonyl benzamide;
N-[(1S,2S,4R)-1-Benzyl-4-cyclohexylcarbamoyl-2-hydroxypentyl]-3-methoxy-5-methylsulfonylpyridine-4-carboxamide;
N-[(1S,2S,4R)-1-Benzyl-4-(bicyclo[2.2.1]hept-2-ylcarbamoyl)-2-hydroxypentyl]3-methylsulfonyl-5-(2-oxopyrrolidin-1-yl)-benzamide;
N-[(1S,2S,4R)-1-Benzyl-4-(bicyclo[2.2.1]hept-2-ylcarbamoyl)-2-hydroxypentyl]-3-methoxy-5-methylsulfonylpyridine-4-carboxamide;

5-Methanesulfonyl-thiophene-2-carboxylic acid [(1S,2S,4R)-1-benzyl-4-(3,3-dimethyl-butylcarbamoyl)-2-hydroxypentyl]-amide;

or a pharmaceutically acceptable salt thereof.

3. A pharmaceutical composition comprising a compound of formula (I) as defined in claim 1 or a pharmaceutically acceptable salt in admixture with one or more pharmaceutically acceptable diluents or carriers.

4. A method for preparing a compound according to claim 1 which method comprises at least one process selected from the group consisting of:

(a) reacting a compound of formula (II)

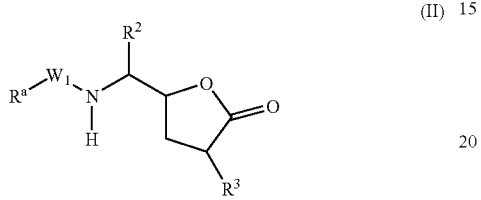

(II)

optionally with any hydroxy or amino groups protected, wherein $R^a$, $R^2$ $R^3$ and $W_1$ are as defined in claim 1, with a compound of formula $R^4$—$NH_2$, wherein $R^4$ is as defined in claim 1, and thereafter optionally deprotecting a compound of formula (I) which is protected;

(b) preparing a compound of formula (I) wherein $W_1$ represents CO which comprises reacting a compound of formula (III)

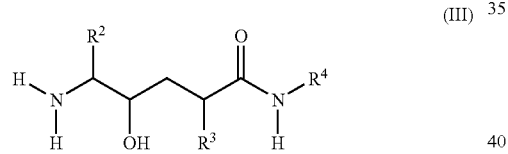

(III)

optionally with any hydroxy or amino groups protected, wherein $R^2$, $R^3$ and $R^4$ are as defined in claim 1, with a compound of formula $R^a$—COOH, or an activated derivative thereof, wherein $R^a$ is as defined in claim 1, and thereafter optionally deprotecting a compound of formula (I) which is protected;

(c) preparing a compound of formula (I) wherein $W_1$ represents $SO_2$ which comprises reacting a compound of formula (III)

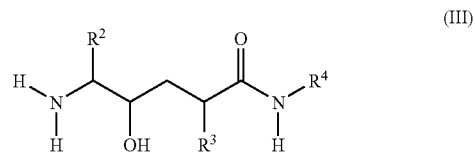

(III)

optionally with any hydroxy or amino groups protected, wherein $R^2$ $R^3$ and $R^4$ are as defined in claim 1, with a compound of formula (IV)

(IV)

or an optionally protected derivative thereof, wherein $R^a$ is as defined in claim 1 and $L^1$ represents a suitable leaving group and thereafter optionally deprotecting a compound of formula (I) which is protected;

(d) deprotecting a compound of formula (I) which is protected; and (e) interconversion of compounds of formula (I) to other compounds of formula (I).

* * * * *

UNITED STATES PATENT AND TRADEMARK OFFICE
CERTIFICATE OF CORRECTION

PATENT NO. : 7,160,905 B2  
APPLICATION NO. : 10/496334  
DATED : January 9, 2007  
INVENTOR(S) : Faller et al.

It is certified that error appears in the above-identified patent and that said Letters Patent is hereby corrected as shown below:

In the Claims:

Column 22 (Lines 8-15 of Claim 1) should read as follows:

or a group of formula (b):

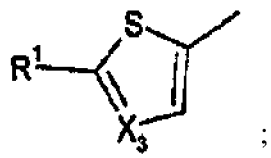

;

$R^1$ represents $-SO_2R^5$;

Signed and Sealed this

Fifth Day of June, 2007

JON W. DUDAS  
*Director of the United States Patent and Trademark Office*